US006294577B1

(12) United States Patent
Vander Meer et al.

(10) Patent No.: US 6,294,577 B1
(45) Date of Patent: Sep. 25, 2001

(54) REPELLENT FOR ANTS

(75) Inventors: Robert K. Vander Meer; William A. Banks; Clifford S. Lofgren, all of Gainesville, FL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/519,179

(22) Filed: Mar. 6, 2000

Related U.S. Application Data

(63) Continuation-in-part of application No. 08/798,162, filed on Feb. 10, 1997, now Pat. No. 6,071,973, which is a continuation of application No. 08/283,115, filed on Jul. 29, 1994, now abandoned, which is a division of application No. 07/925,685, filed on Aug. 7, 1992, now abandoned.

(51) Int. Cl.[7] .......................... A01N 37/02; A01N 37/04
(52) U.S. Cl. ................ 514/547; 514/919; 424/DIG. 10
(58) Field of Search .................................. 514/919, 547; 424/DIG. 10

(56) References Cited

U.S. PATENT DOCUMENTS

| Re. 29,829 | 11/1978 | Bordenca et al. ............... 260/584 |
|---|---|---|
| 2,302,159 | 11/1942 | Wasum ................................ 167/30 |
| 2,971,881 | 2/1961 | Bruce ................................. 167/22 |
| 4,374,991 | 2/1983 | Smolanoff ........................ 546/245 |
| 5,006,562 | 4/1991 | Steltenkamp .................... 514/625 |
| 5,133,959 | 7/1992 | Kumins ............................. 424/84 |
| 5,165,926 | 11/1992 | Wilson et al. ..................... 424/84 |
| 5,221,535 | 6/1993 | Domb ............................... 424/450 |
| 5,721,274 | 2/1998 | Vander Meer et al. .......... 514/532 |

OTHER PUBLICATIONS

Jefson, M., et al., Chemical Defense of a Rove Beetle (*Creophilus maxillosus*), *J. Chemical Ecology*, vol. 9(1), pp. 159–180, 1983.

Honda, H., "Defensive Potential of Components of the Larval Osmeterial Secretion of Papilonid Butterflies Against Ant", *Physiological Entomology*, vol. 8(2), pp. 173–179, Jan. 21, 1983.

Meyers, W., et al., "Polymers Containing Pendent Insecticides",Proc. Int. Symp. *Controlled Release Pestic. Pharm.*, Plenum, NY, pp. 171–190, 1981.

Harris, F., et al., "Polymers Containing Pendent Herbicide Substituents: Hydrolysis Studies II", *American Chemical-Society Symposium Series*, vol. 53, pp. 102–111, 1977.

Cardarelli, N., "New Concepts in the application of Controlled Release Systems to Agriculture", *AmericanChemical Society Symposium Series*, vol. 33, pp. 208–214, 1976.

Vander Meer, R., et al., "Isolation of the Trail Recruitment Pheromone of *Solenopsis invicta*", *J. Chemical Ecology*, vol. 14(3), pp. 825–838, 1988.

King, W.V., "Chemicals Evaluated as Insecticides and Repellents at Orlando, Florida", *U.S. Department of Agriculture, Agriculture Handbook no. 69*, 1954, Washington, DC, pp. 4, 102, and 105.

Schreck, C.E., et al., "Repellents and Other Personal Protection Strategies Against *Aedes albopictus*", *J.American Mosquito Control Assoc.*, vol. 5(2), pp. 247–250, Jun. 1989.

Rutledge, L.C., et al., "Repellent Activity of a Proprietary Bath Oil", *Mosquito News*, (Abstract) vol. 42(4), pp. 557–559, 1982.

*Primary Examiner*—John Pak
(74) *Attorney, Agent, or Firm*—M. Howard Silverstein; John D. Fado; Gail E. Poulos

(57) ABSTRACT

A method and composition has been discovered for repelling ants by treating objects or areas with effective amounts of compositions that includes at least one $C_3$–$C_{10}$ dicarboxylic acid diester and a carrier.

3 Claims, No Drawings

REPELLENT FOR ANTS

This application is a continuation in part of U.S. patent application Ser. No. 08/798,162, filed Feb. 10, 1997, now U.S. Pat. No. 6,071,973; which is a continuation of U.S. patent application Ser. No. 08/283,115, filed Jul. 29, 1994, abandoned; which is a divisional of patent application Ser. No. 07/925,685, filed Aug. 07, 1992 which is abandoned. These three applications are herein incorporated by reference in their entirety.

BACKGROUND OF THE INVENTION

1. Field for the Invention

The present invention relates to repellent compositions for ants, particularly fire ants. The compositions comprise an effective amount of at least one diester of a $C_3$ to $C_{10}$ dicarboxylic acid wherein the ester moieties can be an aliphatic, olefinic, or aryl moieties.

2. Description of the Related Art

Various species of ants post significant problems for man from both an economic and a health care point of view. For example, leaf-cutting ant species are a problem in Central and South America, where they can defoliate a citrus tree overnight. Consequently, a non-toxic repellent that would prevent leaf-cutting ants from getting into the trees would be of significant value. Also, in the southern United States, the fire ant, *Solenopsis invicta*, is a substantial pest. For example, foraging fire ants are known to destroy young citrus trees, growing crops, and germinating seeds. This has an economic impact on agriculture in infested areas. Telephone companies spend substantial amounts of money each year on treating their electrical equipment to prevent fire ant invasion because fire ants accumulate at electrical contacts and can short out electrical equipment. Further, farm equipment can be damaged large fire ant mounds. Fire ants also present a problem to wildlife, such as with ground nesting birds and animals. Furthermore, fire ants are known to excavate the soil from under roadways causing damage.

Fire ants also pose a health care problems to millions of people stung each year—a significant number of which require medical care. Further, fire ant stings are also blamed for human deaths each year. Consequently, there is much interest in controlling these troublesome insects.

This interest has resulted in much research and resources being expended through the years to develop reagents and methods for controlling fire ants. While many useful insecticide formulations have resulted from this research, the problems associated with ants still exist. This is primarily because the relief gained by insecticide use is only temporary owing to the high reproductive capabilities, the efficient foraging behavior, and the ecological adaptability of ants. While effective for controlling ants in relatively small defined areas, the use of insecticides, because of their toxicity, can create other problems. For example, some insecticides, which are effective for controlling ants, are banned from use because they pose a significant threat to the environment, including birds and animals. Furthermore, there is pressure from environmental groups to stop, or at least substantially reduce, the application of insecticides in general, and to develop non-toxic reagents for controlling insects. One type of reagent which would be of great interest would be a non-toxic reagent which could repel, or keep ants from invading a particular area or object.

Such a reagent would be of great value in preventing leaf-cutting ants from attacking citrus and other agriculturally important trees. It would also be of great value for preventing fire ants from attacking various biological control agents, such as parasitic wasps, which are used to control a host of crop pests, including those which are harmful to cotton. The parasitic wasps are distributed as pupae in small capsules which are dispersed in the area to be controlled. Adult wasps emerge from the capsule within a matter of days. If the capsules are distributed in an area infested with fire ants, the capsules are quickly found by foraging ants which penetrate the capsule and eat the wasp in its pupal stage-thus greatly decreasing the effectiveness of the use of such biological control agents.

U.S. patent application Ser. No. 5,721,274 (Vander Meer et al, Issued Feb. 24, 1998; herein incorporated by reference) discloses that Di-(1-methylheptyl) adipate and Bis-(6-methylheptyl) adipate, $C_6$ dicarboxylic acid diesters, show significant repellent activity for fire ants.

Therefore, there is still a substantial need in the art for reagents, particularly non-toxic reagents, which can be used to prevent ants from invading a particular area or object.

SUMMARY OF THE INVENTION

In accordance with the present invention there is provided a repellent composition for ants, which composition is comprised of: (i) an effective amount of at least one diester of a $C_3$ to $C_{10}$ dicarboxylic acid wherein the ester moieties can be an aliphatic, olefinic, acetylenic, or aryl ester moieties and mixtures thereof; and (ii) a carrier material.

Also in accordance with the present invention is a method for repelling ants from an area or object, which method comprises treating said area or object with an effective amount of a repellent composition containing at least one diester of a $C_3$ to $C_{10}$ dicarboxylic acid wherein the ester moieties can be an aliphatic, olefinic, acetylenic, or aryl ester moieties and mixtures thereof and a carrier material.

In a preferred embodiment of the present invention, there is provided an effective amount of the above compositions and a controlled release matrix.

DETAILED DESCRIPTION OF THE INVENTION

In accordance with the present invention there is provided a repellent composition for ants comprised of an effective amount of at least one diester of a $C_3$ to $C_{10}$ dicarboxylic acid wherein the ester moieties can be an aliphatic, olefinic, acetylenic, or aryl ester moieties and mixtures thereof; and (ii) a carrier material. The present invention also relates to a method which includes treating an area or object with an effective amount of at least one diester of a $C_3$ to $C_{10}$ dicarboxylic acid wherein an ester moiety can be an aliphatic, olefinic, acetylenic, or aryl ester moieties and mixtures thereof.

Non-limiting examples of dicarboxylic acid diesters which are suitable for use in the present invention include dimethyl succinate, diethyl adipate, diethyl malonate, diisopropyl adipate, dimethyl adipate, dimethyl 2,5, -dimethyl adipate, dimethyl 2-methyl adipate, diphenyl adipate, dimethyl azelate, dioctyl azelate, dibutyl fumarate, diethyl fumarate, dimethyl fumarate, di-tert-butyl glutarate, diethyl 2-methyl glutarate, dimethyl glutarate, dimethyl 3-phenyl glutarate, 1-ethyl 5- propyl 3 methyl-2-phenyl glutarate, dibutyl maleate, diethyl maleate, diethyl 2-phenyl maleate, dimethyl maleate, dipropyl maleate, di-tert-butyl malonate, butyl ethyl malonate, dibenzyl malonate, diheptyl malonate, dimethy malonate, tert-butyl ethyl malonate tert-butyl methyl malonate, dibutyl sebacate, diethyl sebacate, diethyl sebacate, dimethyl sebacate, dioctyl sebacate, diethyl suberate, dimethyl suberate, (1R) dimenthyl succinate, (1S) dimenthyl succinate, dibenzyl succinate, dibutyl succinate, diocosyl succinate, diethyl succinate, diethyl 2,3-diethyl succinate, diethyl 2,3-diphenyl succinate, diethyl methyl succinate, dimethyl R-methyl succinate, diphenyl succinate, diphenyl succinate, and mixtures thereof.

The amount of repellent used will be at least an effective amount. The term "effective amount" or "amount effective for" as used herein means that minimum amount of repellent needed to repel, or substantially prevent ants from invading a treated area or object, when compared to the same area or object which is untreated. The precise amount needed will vary in accordance with the particular repellent composition used; the type of area or object to be treated; the number of days of repellency needed; and the environment in which the area or object is located. For example, if the object or area to be treated is situated outdoors and is exposed to the weather, then higher concentrations of repellent would be needed to be effective for a given period of time than if the object or area were indoors or under cover. The precise amount of repellent needed can easily be determined by one having ordinary skill in the art given the teachings of this application. The examples herein show typical concentrations which will be needed to repel ants, particularly fire ants.

It is preferred for commercial applications that the repellents of the present invention be applied with a carrier component. The carrier component can be a liquid or a solid material. Liquids suitable as carriers include both water and organic solvents. Non-limiting examples of organic solvents useful in the present invention include acetone, hexane, lacquer, methanol, and methylene chloride. While most of the reagents of the present invention are not particularly soluble in water, they will form a suspension, or emulsion, in water which will be relatively stable and which will be suitable for applying to an area or object to be treated. It is more preferred that the repellent be soluble in the liquid carrier.

Non-limiting examples of solid carrier materials which can be used in the practice of the present invention include diatomaceous earth, alumina, silica, clays, other suitable inorganic oxides, as well as powdered carbohydrates, such as corn starch, dextrans, and cellulose. The carrier may also be a solid substance, preferably one which will slowly release the repellent composition over a period of time. Non-limiting examples of slow release materials which are suitable for use herein include latex particles, capillary tubes, and microencapsulation. The type of area or object to be treated, and the degree of infestation in the vicinity of the area, or object to be treated, will dictate the type of carrier to be used. For example, when the object or area to be treated is a pot containing soil for nursery stock, it is preferred to use an aqueous suspension of the repellent.

The repellent compositions of the present invention can be combined with the solid carrier material by any appropriate means. For example, they may be combined by first dissolving or suspending the repellent in a suitable solvent or other liquid, soaking the solid carrier material with the resulting solution or suspension, thereby either impregnating the repellent into, or depositing it onto, said solid carrier material; and, drying said treated carrier material to drive-off the solvent, or other liquid. The resulting repellent material can then be applied in powder form, for example, by spraying the area or object to be treated.

The following examples are intended to further illustrate the invention and are not intended to limit the scope of the invention as defined by the claims. Fire ants are used as the test model.

EXAMPLE 1

Approximately a 1.0% wt.:vol. hexane solutions were prepared for the diesters of $C_3$ to $C_{10}$ dicarboxylic acids. Each solution was evaluated in a Y-tube olfactometer. The olfactometer used herein is the one described in: Isolation of the Trail Recruitment Pheromone of *Solenopsis invicta*, by R. K. Vander Meer, F. Alvarez, and C. S. Lofgren, Journal of Chemical Ecology, Volume 14, No. 3, pages 825–838, 1988, and which is herein incorporated by reference.

The Y-tube olfactometer is comprised of two 24/40 ground glass joints wherein each ring is sealed to one of the arms of a male half of one of the ground glass joints. A 5 cm piece of 0.6 cm ID tubing is ring sealed 1 cm into the female half of the ground glass joints. A baffle is provided at the center of the Y-tube for controlling air streams and to prevent premature mixing of the sample. It also gives the ants a clearer choice. The baffle also narrows the openings to the choice chambers to the minimum size required for passage of a major ant worker. A test sample (10 μl if a 1% hexane solution) and a solvent blank (10 μl hexane) were each applied to a separate filter paper strip (approximately 0.3×2.0 cm, Whatman NO. 1). Each was air dried and one was placed in one of the choice chambers and the other in the other chamber. Compressed air (breathing air quality) was split into two streams and passed into the two chambers. Each stream was regulated to about 0.2 liters/min. For a total effluent flow rate of about 0.4 liters/min. Approximately 50 to 70 ants from laboratory colonies were confined in a 2.5 cm piece of 0.9 cm ID TYGON tubing which was sealed at one end with wire guaze. The open end of the tubing was attached to the entrance stem leading to both chambers.

The initial choice of the first twenty ants that walked down the entrance tube and into one of the arms (chambers) of the Y-tube was recorded. Ants that were not trapped in a chamber and came back to the entrance stem were not counted if they made another choice. After each test, the olfactometer was rinsed with acetone and dried. Each test sample was retested with worker ants from the same colony, but the choice chamber in which the sample and control were placed was reversed. This procedure eliminated any bias inherent in the olfactometer. A complete replicate was the sum of the results from three tests. Data were analyzed by a chi-squared test. The results are shown in Table 1 below.

TABLE 1

| COMPOUND | % RESPONSE |
| --- | --- |
| Dibutyl Sebacate | 50.83; SD = 5.2; SE = 3.01 |
| Dimethyl Succinate | 3.33; SD = 1.44; SE = 0.83 |
| Diethyl Adipate | 5.83; SD = 2.89; SE = 1.67 |
| Diethyl Malonate | 25.80; SD = 1.40; SE = 0.80 |

Solutions which received about 35% or less response are considered repellents, and those between about 35% and 65% are considered neutral. Solutions which received greater than about a 65% response are considered attractants.

The foregoing detailed description is for the purpose of illustration. Such detail is solely for that purpose and those skilled in the art can make variations therein without departing from the spirit and scope of the invention.

What is claimed is:

1. A method for repelling ants from an object or an area comprising treating the object or area with an ant repelling composition comprising:

(a) an ant repellent agent selected from the group consisting of dimethyl succinate, diethyl adipate, diethyl malonate, and mixtures thereof; and
   (b) a carrier material.

2. The method of claim 1 wherein the carrier is an organic solvent selected from the group consisting of acetone, hexane, methanol, methylene chloride, and lacquer.

3. The method of claim 1 wherein the carrier is a solid carrier.

* * * * *